US00PP34717P2

(12) United States Plant Patent
Shoup

(10) Patent No.: US PP34,717 P2
(45) Date of Patent: Nov. 8, 2022

(54) SHRUB ROSE PLANT NAMED 'COLOGNE KING'

(50) Latin Name: *Rosa hybrida*
Varietal Denomination: 'Cologne King'

(71) Applicant: George Michael Shoup, Brenham, TX (US)

(72) Inventor: George Michael Shoup, Brenham, TX (US)

( * ) Notice: Subject to any disclaimer, the term of this patent is extended or adjusted under 35 U.S.C. 154(b) by 88 days.

(21) Appl. No.: 17/350,691

(22) Filed: Jun. 17, 2021

(51) Int. Cl.
*A01H 5/02* (2018.01)
*A01H 6/74* (2018.01)

(52) U.S. Cl.
USPC ..... Plt./107
CPC ..... *A01H 6/74* (2018.05)

(58) Field of Classification Search
USPC ..... Plt./107
CPC ..... A01H 5/02
See application file for complete search history.

*Primary Examiner* — Kent L Bell

(57) ABSTRACT

A new and distinct variety of shrub rose plant, referred to by its cultivar name, 'Cologne King', is provided which continuously forms exceedingly fragrant blooms throughout the growing season. The growth habit is upright and continuously produces glabrous canes. The foliage is, matte, and medium green. The plant propagates from cuttings easily and has resistance to blackspot. The new variety is well suited to growing in the landscape as a specimen plant where its fragrant blooms can be enjoyed, especially in areas designated for children or the elderly due to its prickle-free "thornless" nature.

1 Drawing Sheet

Botanical/commercial classification:
Latin name: *Rosa hybrida.*
Varietal denomination: 'Cologne King'.

SUMMARY OF THE INVENTION

The new variety of *Rosa hybrida* shrub rose plant was created at Brenham, Tex., U.S.A., by artificial pollination wherein two parents were crossed which previously had been observed in the hope that they would contribute their unique fragrance (from the female parent), and glabrous stems and fragrance (in the case of the male parent). The female parent (i.e., the seed parent) was the 'Meiclusif' variety (non-patented in the United States). The male parent (i.e., the pollen parent) was the 'Southern Damask' variety (non-patented). The male parent variety is a seedling from the breeding program that is not yet publicly available. The parentage of the male parent variety, 'Southern Damask' can be summarized as follows: 'Thomas Affleck' (non-patented) x 'Autumn Damask' (non-patented).

The parentage of the new variety can be summarized as follows:

'Meiclusif' x 'Southern Damask'

The seeds resulting from the above pollination were stratified in an artificial environment and sown into trays in a greenhouse environment. Seedlings were obtained and displayed phenotypic and biological variation. Selective trialing and evaluation of the seedlings resulted in the identification of a single plant of the new variety.

It was found that the new shrub rose plant of the present invention possesses the following combination of characteristics:

(a) continuously blooms throughout the growing season,
(b) forms vegetation and stems that are lacking,
(c) exhibits resistance to blackspot, (d) forms blooms that are exceedingly fragrant,
(e) is well suited for growing as attractive ornamentation and source of fragrance in the landscape.

The new rose can be readily distinguished from its ancestors upon inspecting the blossoms. More specifically, the 'Cologne King' variety forms dissimilar dark pink blossoms when compared with the parental variety 'Southern Damask', which forms very light pink blossoms. Additionally, the new variety can also be distinguished from its ancestors by inspecting the fragrance of the blossoms. More specifically, the 'Cologne King' variety forms blossoms of a dissimilar damask rose fragrance when compared with the parental variety 'Meiclusif', which forms blossoms of a citrus fragrance.

The new variety of the present invention also can be readily distinguished from other shrub rose plants, including the 'Auscot' variety (U.S. Plant Pat. No. 7,215) upon inspection of the stems. More specifically, the 'Cologne King' variety forms dissimilar glabrous stems which are absent of prickles when compared to the 'Auscot' variety which forms stems containing prickles.

Asexual reproduction of 'Cologne King' was done by taking cuttings in Brenham Tex., U.S.A. in beginning in 2019. Cuttings were taken from mature stems that were approximately 10 to 15 cm in length and approximately 0.75 cm in diameter. Initial cuttings were taken of the new variety and grew into mature plants. Subsequent cuttings were taken of the initial asexually reproduced plants and grown into mature plants. Mature plants of both the initially propagated plants and the subsequently propagated plants were compared. There was no observable difference between the generations. Therefore, it was demonstrated that the characteristics of 'Cologne King' remain stable, uniform, and true to type in successive generations of asexual reproduction.

BRIEF DESCRIPTION OF THE DRAWING

The accompanying color illustration shows as true as is reasonably possible to obtain in color photographs of this type, the typical characteristics of the plant parts, i.e., the flowers, buds, stems and leaves of the new rose, 'Cologne King'. The illustrated rose plant parts were approximately one year of age and were observed during August, while growing on their own roots in Brenham, Tex., U.S.A. Flowers, buds, and stem growth are displayed in various stages of maturity. The upper side and under side of the leaves, blooms and petals are displayed.

DETAILED BOTANICAL DESCRIPTION

The chart used in the identification of colors is The Royal Horticultural Society Colour Chart (R.H.S. Colour Chart) Edition V (2007). The description is based one year old specimens of the new variety during August while growing outdoors on their own roots at Brenham, Tex., U.S.A.

Class: Shrub Rose. Cultivar 'Cologne King'.

Plant:

*Height*.—Approximately 1.2 to 1.5 meters on average at maturity.

*Width*.—Approximately 0.9 to 1.2 meters on average at maturity.

*Habit*.—Upright.

Stems:

*Size*.—Approximately 18 cm tall by 1 cm in caliper.

*Color*.—Young stems: Yellow-Green Group 147A to 147B. Adult wood: Yellow-Green Group 146B to 146C.

*Prickles*.—Size: N/A. Quantity: Absent. Size: N/A. Color: N/A. Density: N/A.

*Texture*.—Glabrous.

*Internodal spacing*.—Approximately 6 cm on average.

Leaves:

*Arrangement*.—Alternate, odd-pinnate, and compound.

*Margin*.—Serrate.

*Stipules*.—Size: Approximately 2 cm×0.5 cm on average. Margin: Adnate with winged tips and entire edges. Color: Green Group 141A. Texture: Glabrous.

*Size*.—Approximately 16.5 cm×10.5 cm on average.

*Petioles*.—Upper surface: Yellow-Green Group 146B. Under surface: Green Group 140A to 140B. Size: Approximately 7 cm×1.5 mm on average. Shape: Filiform.

*Glossiness of the upper side of the leaf*.—Medium.

*Rachis*.—Color: Green Group 140A to 140B.

*Leaflets*.—Number: 5 and 7. Shape: Ovate, with obtuse apex and obtuse base. Size: Approximately 5.25 cm×3.75 cm on average. Venation: Reticulate. Venation Color: Green Group 141A. Apex: Acute. Base: Obtuse. Overall appearance: Green, leathery, and semi-glossy. Undulation of Margin: Medium. Texture Upper Surface: Smooth. Texture Under Surface: Matte. Color (young foliage) upper surface: Brown Group 200A to 200B. Color (young foliage) under surface: Brown Group 200B to 200C. Color (adult foliage) upper surface: Green Group 141A. Color (adult foliage) under surface: Green Group 138A.

Inflorescence:

*Average size of inflorescence*.—Approximately 15 cm by 12 cm on average.

*Number of flowers per inflorescence*.—Approximately 1 on average.

*Florescence type*.—Singular.

*Peduncle*.—Color: Yellow-Green Group 143A. Length: Approximately 4.8 cm in length on average. Width: 2.1 mm in width on average. Texture: Glabrous.

*Sepals*.—Number: 5. Size: Approximately 2 cm×0.8 cm on average. Arrangement: Pentamerous and imbricate. Shape: Obcunate. Margin: Entire. Sepal Extensions: Weak. Apex: Acuminate. Base: Truncate. Texture: Glabrous. Upper surface: Green Group 143A. Under surface: Green Group 143C.

*Buds*.—Shape: Ovoid to slender with pointed apex. Size: Approximately 3.5 cm in length and 1.5 cm in width on average. Color (when opening) upper surface: Yellow-Orange Group 14B to 14C at the base of the bud, transitioning to Red-Purple Group 67A, transitioning to Red-Purple Group 66A, and then finally to Red-Purple Group N57A. Color (when opening) under surface: Red-Purple Group 67B at the base of the bud, transitioning to Red Group 51B.

Flower:

*Form*.—Open cup to occasional rosette.

*Shape*.—Flattened orbicular when open.

*Profile of the lower part of the flower*.—Convex.

*Diameter*.—Approximately 9cm on average.

*Color*.—(when opening) upper surface: Red-Purple Group N74A to N74B. (when opening) under surface: Red-Purple Group N74B to N74C. (when blooming) upper surface: Red-Purple Group N74B. (when blooming) under surface: Red-Purple Group 68B. (end of blooming) upper surface: Red-Purple Group N74C to N74D. (end of blooming) under surface: Red-Purple Group 68B.

*Fragrance*.—Cherry and damask with hints of citrus.

*Petals*.—Petal Size: Approximately 3 cm×3.5 cm on average. Petal Shape — Obcordate. Petal Number — Approximately 25 on average. Petaloids: None present. Petal Drop: Very easily and cleanly after blooming. Apex: Chordate. Base: Acute. Margin: Entire. Texture: Glabrous. Basal Spot: Absent.

*Stamen number*.—Sparse. Approximately 141 on average.

*Anther color*.—Yellow Group 13B.

*Anther shape*.—Subobtuse.

*Anther length*.—Approximately 4 mm on average.

*Filament color*.—Yellow-Orange Group 15C.

*Filament length*.—Approximately 3 mm on average.

*Pollen quantity*.—Medium amount of pollen produced.

*Pollen color*.—Yellow Group 13C.

*Pistil form*.—Separate and very free, but tightly packed together.

*Pistil number*.—Approximately 82 on average.

*Stigma color*.—Yellow-Orange Group 22C.

*Style color*.—Yellow-Orange Group 19B.

*Style length*.—Approximately 0.5 cm on average.

*Receptacle*.—Achenes located on the bottom and walls inside the fruit. Size: Approximately 1 cm×0.6 cm on average when mature.

*Rate of flower opening*.—Fast.

*Blossoming*.—Continuous.

*Lasting quality*.—On plant: Approximately 3 to 4 days on average. In vase: Unknown.

Development:

*Vegetation*.—Average vigor.

*Growth rate*.—Slow.

*Hip/seed formation*.—A medium number of hips are formed after blossoming.

Root system:

*Root color*.—Yellow-White Group 158B.

*Root habit*.—Well rounded.

Physiology:

*Disease resistance*.—Resistant to some races of *Diplocarpon rosae* (Black Spot), and above average resistance to *Podosphaera pannosa* (Powdery Mildew).

*Cold hardiness*.—The variety has been found to be suitable for climactic conditions in USDA Plant Hardiness Zone 8. Based on the performance of the parental varieties, it is likely, although untested, that the new variety is also suitable for climatic conditions of USDA Plant Hardiness Zones 5, 6 and 7.

*Heat tolerance*.—The variety exhibits average heat tolerance. The variety has been found to be suitable for climactic conditions in USDA Plant Hardiness Zone 8. Based on the performance of its parent varieties, it is likely, although untested, that the new variety is also suitable for climatic conditions of USDA Plant Hardiness Zone 9.

*Drought tolerance*.—The variety exhibits average drought tolerance.

I claim:

1. A new and distinct shrub rose plant named 'Cologne King' characterized by the following combination of characteristics:

1) continuously blooms throughout the growing season,
2) forms vegetation and stems that are lacking,
3) exhibits resistance to blackspot,
4) forms blooms that are exceedingly fragrant,
5) is well suited for growing as attractive ornamentation and source of fragrance in the landscape.

substantially as herein illustrated and described.

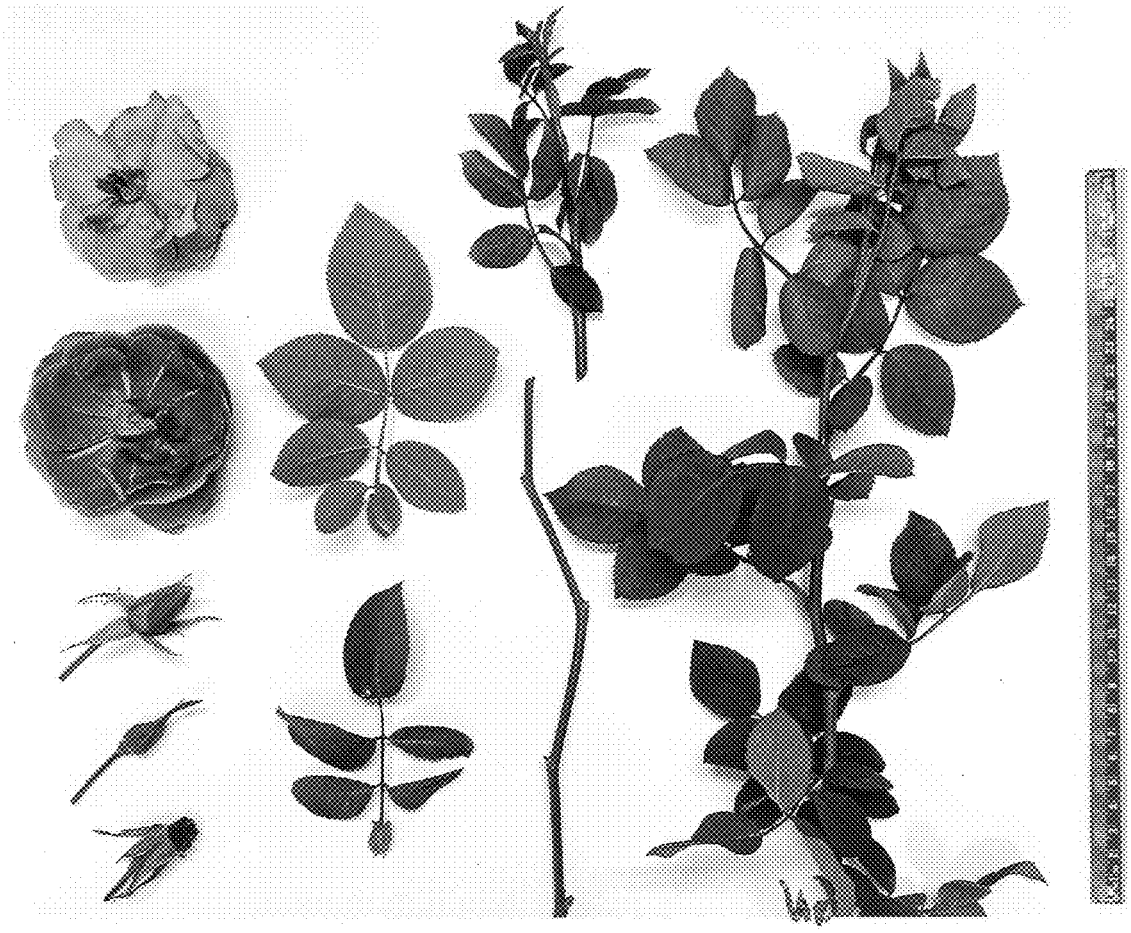

* * * * *